(12) United States Patent
Chia et al.

(10) Patent No.: US 12,144,812 B2
(45) Date of Patent: Nov. 19, 2024

(54) FORMULATIONS OF PYRIMIDINE CYCLOHEXYL GLUCOCORTICOID RECEPTOR MODULATORS

(71) Applicant: CORCEPT THERAPEUTICS INCORPORATED, Menlo Park, CA (US)

(72) Inventors: Yip-Fong Chia, Menlo Park, CA (US); Stephen Arboleda, Menlo Park, CA (US); Yan Alsmeyer, Menlo Park, CA (US); Gordon Davis, Menlo Park, CA (US); Tyler Clikeman, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 126 days.

(21) Appl. No.: 17/308,376

(22) Filed: May 5, 2021

(65) Prior Publication Data
US 2021/0361651 A1    Nov. 25, 2021

Related U.S. Application Data

(60) Provisional application No. 63/020,919, filed on May 6, 2020.

(51) Int. Cl.
*A61K 31/513*    (2006.01)
*A61K 9/20*    (2006.01)

(52) U.S. Cl.
CPC .......... *A61K 31/513* (2013.01); *A61K 9/2009* (2013.01); *A61K 9/2013* (2013.01); *A61K 9/2027* (2013.01); *A61K 9/2054* (2013.01); *A61K 9/2095* (2013.01)

(58) Field of Classification Search
CPC .................................................. A61K 31/513
See application file for complete search history.

(56) References Cited

U.S. PATENT DOCUMENTS

| | | | |
|---|---|---|---|
| 6,852,719 B2 | 2/2005 | Liu et al. | |
| 7,576,076 B2 | 8/2009 | Clark et al. | |
| 7,799,782 B2 | 9/2010 | Munson et al. | |
| 8,173,664 B2 | 5/2012 | Clark et al. | |
| 8,685,973 B2 | 4/2014 | Clark et al. | |
| 8,906,917 B2 | 12/2014 | Clark et al. | |
| 9,321,736 B2 | 4/2016 | Clark et al. | |
| 9,622,979 B2 | 4/2017 | Bhavarisetti et al. | |
| 9,626,979 B2 | 4/2017 | Sung et al. | |
| 10,238,659 B2 * | 3/2019 | Belanoff | A61K 31/513 |
| 10,881,660 B2 | 1/2021 | Belanoff et al. | |
| 11,542,238 B2 | 1/2023 | Hunt et al. | |
| 11,548,856 B2 | 1/2023 | Hunt et al. | |
| 11,760,731 B2 | 9/2023 | Hunt | |
| 2007/0155707 A1 * | 7/2007 | Dasse | C07C 271/44 548/253 |
| 2010/0267643 A1 * | 10/2010 | Baron | A61P 3/06 514/23 |
| 2021/0238148 A1 | 8/2021 | Hunt et al. | |
| 2021/0363112 A1 | 11/2021 | Hunt et al. | |
| 2023/0183186 A1 | 6/2023 | Hunt et al. | |
| 2023/0212128 A1 | 7/2023 | Hunt et al. | |
| 2024/0083856 A1 | 3/2024 | Hunt et al. | |

FOREIGN PATENT DOCUMENTS

| | | |
|---|---|---|
| EP | 0037495 A1 | 10/1981 |
| EP | 0369627 A2 | 5/1990 |
| EP | 0722732 A1 | 7/1996 |
| EP | 2313212 A1 | 4/2011 |
| JP | H06128238 A | 5/1994 |
| JP | H1017555 A | 1/1998 |
| JP | 2000271618 A | 10/2000 |
| WO | 0244120 A1 | 6/2002 |
| WO | 2003/009853 | 2/2003 |
| WO | 03084935 A2 | 10/2003 |
| WO | 2005105036 A1 | 11/2005 |
| WO | 2009014141 A1 | 1/2009 |
| WO | 2010052445 A1 | 5/2010 |
| WO | 2011132094 A2 | 10/2011 |
| WO | 2012129074 A1 | 9/2012 |
| WO | 2016061195 A1 | 4/2016 |
| WO | 2018236749 A2 | 12/2018 |
| WO | 2019220282 A1 | 11/2019 |
| WO | 2019236487 A1 | 12/2019 |
| WO | 2020190351 A1 | 9/2020 |
| WO | 2021226260 A1 | 11/2021 |
| WO | 2022140293 A9 | 6/2022 |

OTHER PUBLICATIONS

Shin-Etsu Document (https://www.setylose.com/en/products/healthcare/shinetsu-aqoat) (Year: 2023).*
Sester et al. (pH-Sensitive methacrylic acid-methyl methacrylate copolymer Eudragit L100 and dimethylaminoethyl methacrylate, butyl methacrylate, and methyl methacrylate tri-copolymer Eudragit E100, HAL, 2020). (Year: 2020).*
https://www.pharmaexcipients.com/product/eudragit-l-100/ (Year: 2023).*
International Search Report and Written Opinion issued in related International Patent Application No. PCT/ US2019/035229, mailed on Oct. 1, 2019, 10 pages.
International Search Report and Written Opinion issued in related International Patent Application. No. PCT/US2005/023675, mailed on Dec. 13, 2005, 11 pages.
International Search Report and Written Opinion issued in related International Patent Application. No. PCT/US2012/029376, mailed on Jun. 27, 2012, 8 pages.

(Continued)

*Primary Examiner* — Andrew S Rosenthal
*Assistant Examiner* — Danielle Kim
(74) *Attorney, Agent, or Firm* — Mintz, Levin, Cohn, Ferris, Glovsky and Popeo, P.C.

(57) ABSTRACT

The present invention provides formulations of (E)-6-(4-Phenylcyclohexyl)-5-(3-trifluoromethylbenzyl)-1H-pyrimidine-2,4-dione, and methods of making and using the same.

15 Claims, 6 Drawing Sheets

(56) References Cited

OTHER PUBLICATIONS

U.S. Appl. No. 17/308,380, filed May 5, 2021, "Polymorphs of Pyrimidine Cyclohexyl Glucocorticoid Receptor Modulators", 88 pages.
Ali et al. (Apr. 2, 2004) "Novel N-Arylpyrazolo[3,2-c]-Based Ligands for the Glucocorticoid Receptor: Receptor Binding and in Vivo Activity", J. Med. Chem., 47(10):2441-2452.
Baptista (Jul. 1999) "Body Weight Gain Induced by Antipsychotic Drugs: Mechanisms and Management", Acta Psychiatr Scand, 100(1):3-16.
Bertagna et al. (Jul. 1984) "The New Steroid Analog RU 486 Inhibits Glucocorticoid Action in Man", J Clin Endocrinol Metab, 59(1):25-28.
Bhuyan et al. (1998) "Studies on Uracils: Synthesis of Novel Uracil Analogues via 1,5- and 1,6-Intramolecular Cycloaddition Reactions", Journal of Chemical Research, Synopses, 9:502-503.
Bledsoe et al. (Jul. 12, 2002) "Crystal Structure of the Glucocorticoid Receptor Ligand Binding Domain Reveals a Novel Mode of Receptor Dimerization and Coactivator Recognition", Cell, 110(1):93-105.
Brophy et al. (Jan. 1983) "Bioavailability of Oral Dexamethasone During High Dose Steroid Therapy in Neurological Patients", European Journal of Clinical Pharmacology, 24:103-108.
Cadepond et al. (1997) "RU486 (mifepristone): Mechanisms of Action and Clinical Uses", Annu Rev Med, 48:129-156.
Dorwald Florencioz. (2005) "Side Reactions in Organic Synthesis: A Guide to Successful Synthesis Design", Wiley, VCH, Weinheim p. IX of Preface.
Eyles et al. (Jul. 1997) "Oral Delivery and Fate of Poly(Lactic Acid) Microsphere-Encapsulated Interferon in Rats", Journal of Pharmacy and Pharmacology, 49(7):669-674.
Fotherby (Aug. 1996) "Bioavailability of Orally Administered Sex Steroids Used in Oral Contraception and Hormone Replacement Therapy", Contraception, 54(2):59-69.
Fukazawa et al. (1998) "6-Amino-5-Methyluracil Derivatives and Their Use as Thymidine Phosphorylase Inhibitors and Neovascularization Inhibitors", XP002355358; Database CA 'Online'; Chemical Abstracts Service, Columbus, OH, US; Database Accession No. 1998:59356. (English Abstract Submitted.).
Gao et al. (Jun. 1995) "Controlled Release of a Contraceptive Steroid from Biodegradable and Injectable Gel Formulations: In Vitro Evaluation", Pharmaceutical Research, 12(6):857-863.
Groning et al. (May 1996) "Three-dimensional Solubility Parameters and Their Use in Characterising the Permeation of Drugs Through the Skin", Pharmazie, 51(5):337-341.
Hidalgo-Aragones et al. (Aug. 1996) "Pharmacokinetics of oestrone-3-O-sulphamate", The Journal of Steroid Biochemistry and Molecular Biology, 58(5-6):611-617.
Hunt et al. (Dec. 15, 2012) "Discovery of a Novel Non-steroidal GR Antagonist With in Vivo Efficacy in the Olanzapine-induced Weight Gain Model in the Rat", Bioorganic & Medicinal Chemistry Letters, 22(24):7376-7380.
Johnson et al. (Sep. 1995) "Permeation of Steroids through Human Skin", Journal of Pharmaceutical Sciences, 84(9):1144-1146.
Minto et al. (Apr. 1, 1997) "Pharmacokinetics and Pharmacodynamics of Nandrolone Esters in Oil Vehicle: Effects of Ester, Injection Site and Injection Volume", The Journal of Pharmacology and Experimental Therapeutics, 281(1):93-102.
Nguyen et al. (Sep. 1, 2017) "A Mixed Glucocorticoid/mineralocorticoid Receptor Modulator Dampens Endocrine and Hippocampal Stress Responsivity in Male Rats", Physiology & Behavior, 178:82-92.
Rao K. Paduranga (1995) "Recent Developments of Collagen-Based Materials for Medical Applications and Drug Delivery Systems", Journal of Biomaterials Science, Polymer Edition, 7(7):623-645.
Rohatagi et al. (1995) "Pharmacokinetic and Pharmacodynamic Evaluation of Triamcinolone Acetonide After Intravenous, Oral, and Inhaled Administration", Journal of Clinical Pharmacology, 35(12):1187-1193.
Rohatagi et al. (Sep. 1, 1995) "Pharmacokinetic Interaction Between Endogenous Cortisol and Exogenous Corticosteroids", Die Pharmazie, 50(9):610-613.
Teutsch et al. (Nov. 1, 1991) "Design of Ligands for the Glucocorticoid and Progestin Receptors", Biochemical Society Transactions, 19(4):901-908.
Tjwa et al. (1995) "Budesonide Inhaled Via Turbuhaler: A More Effective Treatment for Asthma than Beclomethasone Dipropionate Via Rotahaler", Annals of Allergy, Asthma & Immunology, 75(2):107-111.
Turner et al. (Oct. 2005) "Structure of the glucocorticoid receptor (NR3C1) gene 5' untranslated region: dentification, and tissue distribution of multiple new human exon 1", J Mol Endocrinol, 5(2):283-292.
Umbricht et al. (Sep. 1994) "Clozapine and Weight Gain", J Clin Psychiatry, 55 Suppl B:157-160.
U.S. Appl. No. 17/556,786, filed Dec. 20, 2021, Dener et al.
International Search Report and Written Opinion received for PCT Application No. PCT/US2021/030923, mailed on Aug. 18, 2021, 13 pages.
International Search Report and Written Opinion received for PCT Application No. PCT/US2021/030925, mailed on Aug. 20, 2021, 14 pages.
Koorneef et al. (2018) "Selective Glucocorticoid Receptor Modulation Prevents and Reverses Nonalcoholic Fatty Liver Disease in Male Mice", Endocrinology, 159(12):3925-3936.
Lee et al. (2020) "Reversal of Antipsychotic-induced Weight Gain in Rats with Miricorilant, A Selective Glucocorticoid Receptor (Gr) Modulator", American Psychiatric Association Annual Meeting, 1 Page.
Hilton et al., Journal of Pharmaceutical Sciences, 82(7): 737-743, Jul. 1993 (Abstract).
Butreddy, "Hydroxypropyl methylcellulose acetate succinate as an exceptional polymer for amorphous solid dispersion formulations: A review from bench to clinic" European Journal of Pharmaceutics and Biopharmaceutics 177:289-307, 2022.

* cited by examiner

FIG. 2. Compound I Form B, XRPD Peak Table

| Angle/° 2θ | Rel. Int. [%] |
|---|---|
| 4.32 | 2.38 |
| 8.95 | 2.56 |
| 9.51 | 2.33 |
| 9.83 | 10.41 |
| 10.37 | 7.7 |
| 10.58 | 4.96 |
| 11.21 | 5.73 |
| 11.77 | 5.49 |
| 13.01 | 4.1 |
| 13.40 | 21.04 |
| 13.69 | 7.35 |
| 14.03 | 4.49 |
| 14.33 | 4.4 |
| 14.78 | 13.64 |
| 15.43 | 1.41 |
| 15.79 | 24.83 |
| 16.20 | 23.89 |
| 16.56 | 8.57 |
| 16.73 | 35.51 |
| 17.03 | 74.86 |
| 17.32 | 67.69 |
| 17.74 | 55.03 |
| 18.01 | 22.65 |
| 18.38 | 2.08 |
| 19.00 | 100 |
| 19.62 | 33.42 |
| 20.25 | 6.13 |
| 20.45 | 10.29 |
| 20.83 | 5.76 |
| 21.03 | 7.87 |
| 21.32 | 24.22 |
| 21.76 | 2.85 |
| 22.01 | 5.69 |
| 22.28 | 5.32 |
| 22.67 | 9.05 |
| 23.06 | 3.04 |
| 23.40 | 2.79 |
| 23.60 | 28.64 |
| 23.80 | 6.1 |
| 24.07 | 3.82 |
| 24.36 | 11.39 |
| 25.37 | 7.56 |
| 25.58 | 6.27 |
| 25.74 | 24.12 |
| 26.31 | 5.21 |
| 26.51 | 3.4 |
| 26.78 | 3.92 |
| 27.10 | 3.01 |
| 27.36 | 2.53 |
| 27.84 | 2.68 |
| 28.12 | 5.39 |
| 28.70 | 5.42 |
| 29.41 | 2.11 |
| 29.67 | 2.41 |
| 29.86 | 3.22 |
| 30.85 | 1.43 |
| 31.33 | 2.86 |
| 31.87 | 3.29 |
| 31.99 | 3.51 |
| 32.36 | 1.27 |
| 32.77 | 2.39 |
| 33.95 | 4.75 |
| 34.26 | 3.51 |
| 34.49 | 1.73 |
| 35.05 | 1.59 |
| 35.53 | 3.27 |
| 36.39 | 1.8 |
| 36.60 | 3.84 |
| 37.24 | 5.15 |
| 37.72 | 2.22 |
| 38.55 | 2.35 |
| 39.05 | 2.32 |

Compound I Form B, DSC & TGA Thermogram

Dissolution Graph

FIG. 6

| TREATMENT | SUBJID | AUC0-24 (h*ng/mL) | AUClast (h*ng/mL) | AUCinf (h*ng/mL) | Cmax (ng/mL) | Tmax (h) |
|---|---|---|---|---|---|---|
| New C1 Tablets | 1001 | 1454 | 1454 | 1516 | 228 | 2 |
| | 1002 | 520 | 658 | 745 | 65 | 2 |
| | 1003 | 4873 | 5132 | 5176 | 665 | 2 |
| | 1004 | 2683 | 2912 | 2994 | 401 | 4 |
| | Mean | 2382 | 2539 | 2608 | 340 | 3 |
| | CV% | 79 | 77 | 75 | 76 | 40 |
| | Geometric Mean | 1773 | 1945 | 2046 | 251 | 2 |
| | Geometric CV% | 122 | 109 | 101 | 131 | 36 |
| New D3 Tablets | 1001 | 16988 | 18244 | 18295 | 1750 | 4 |
| | 1002 | 5093 | 5716 | 5794 | 561 | 4 |
| | 1003 | 16803 | 18238 | 18346 | 1810 | 4 |
| | 1004 | 25625 | 27642 | 27905 | 2050 | 4 |
| | Mean | 16127 | 17460 | 17585 | 1543 | 4 |
| | CV% | 52 | 52 | 52 | 43 | 0 |
| | Geometric Mean | 13893 | 15142 | 15262 | 1382 | 4 |
| | Geometric CV% | 79 | 76 | 76 | 66 | 0 |
| New E1 Tablets | 1001 | 7943 | 8982 | 9041 | 646 | 8 |
| | 1002 | 5242 | 6256 | 6460 | 408 | 4 |
| | 1003 | 10332 | 11406 | 11435 | 933 | 4 |
| | 1004 | 8497 | 10818 | 11746 | 652 | 4 |
| | Mean | 8003 | 9366 | 9670 | 660 | 5 |
| | CV% | 26 | 25 | 25 | 33 | 40 |
| | Geometric Mean | 7775 | 9125 | 9411 | 633 | 5 |
| | Geometric CV% | 29 | 28 | 28 | 35 | 36 |

FIG. 7

| Test Article | Treatment Name | Dose (mg) | Animal ID | AUC$_{0-24}$ (h*ng/mL) | AUC$_{last}$ (h*ng/mL) | AUC$_{inf}$ (h*ng/mL) | AUC$_{\%exp}$ (%) | C$_{max}$ (ng/mL) | T$_{max}$ (h) | T$_{last}$ (h) |
|---|---|---|---|---|---|---|---|---|---|---|
| 3 X 100 mg immediate release tablets | Original 100 mg tablets | 300 | 1001M | 7,983 | 9,305 | 9,390 | 0.90 | 518 | 12 | 48 |
| | | | 1002M | 646 | 646 | 837 | 22.80 | 59 | 2 | 24 |
| | | | 1003M | 2,174 | 2,449 | 2,514 | 2.60 | 236 | 4 | 48 |
| | | | 1004M | 1,924 | 2,138 | 2,183 | 2.00 | 256 | 2 | 48 |
| | | | Geometric Mean | 2,155 | 2,369 | 2,563 | 3.20 | 207 | 2 | 40 |
| | | | Geometric CV% | 137 | 151 | 130 | 238 | 113 | 102 | 36 |
| 1 X 300 mg immediate release tablet | Lonza C1 300mg tablet | 300 | 1001M | 16,151 | 20,573 | 21,173 | 2.80 | 1,120 | 8 | 48 |
| | | | 1002M | 932 | 1,132 | 1,178 | 3.90 | 86 | 2 | 48 |
| | | | 1003M | 4,307 | 4,886 | 4,966 | 1.60 | 408 | 4 | 48 |
| | | | 1004M | 1,746 | 1,948 | 2,002 | 2.70 | 237 | 4 | 48 |
| | | | Geometric Mean | 3,262 | 3,859 | 3,968 | 2.60 | 311 | 4 | 48 |
| | | | Geometric CV% | 190 | 200 | 199 | 38 | 147 | 61 | 0 |
| 1 X 300 mg immediate release tablet | Lonza D2 300mg tablet | 300 | 1001M | 9,494 | 10,646 | 10,715 | 0.60 | 660 | 4 | 48 |
| | | | 1002M | 5,053 | 5,774 | 5,994 | 3.70 | 463 | 4 | 48 |
| | | | 1003M | 3,836 | 4,565 | 4,763 | 4.20 | 339 | 4 | 48 |
| | | | 1004M | 3,979 | 4,458 | 4,518 | 1.30 | 382 | 4 | 48 |
| | | | Geometric Mean | 5,202 | 5,947 | 6,097 | 1.90 | 446 | 4 | 48 |
| | | | Geometric CV% | 44 | 42 | 41 | 109 | 30 | 0 | 0 |
| 2 X 150 mg immediate release tablets | Lonza D3 150mg tablets | 300 | 1001M | 12,685 | 13,689 | 13,962 | 2.00 | 1,490 | 4 | 48 |
| | | | 1002M | 6,091 | 8,142 | 8,304 | 2.00 | 407 | 4 | 48 |
| | | | 1003M | 8,725 | 10,373 | 10,476 | 1.00 | 575 | 8 | 48 |
| | | | 1004M | 5,620 | 6,178 | 6,233 | 0.90 | 502 | 4 | 48 |
| | | | Geometric Mean | 7,846 | 9,193 | 9,328 | 1.30 | 647 | 5 | 48 |
| | | | Geometric CV% | 39 | 35 | 35 | 45 | 62 | 36 | 0 |

FORMULATIONS OF PYRIMIDINE CYCLOHEXYL GLUCOCORTICOID RECEPTOR MODULATORS

CROSS-REFERENCE TO RELATED APPLICATIONS

This application claims priority to U.S. Provisional Application No. 63/020,919, filed May 6, 2020, which is incorporated herein in its entirety for all purposes.

BACKGROUND

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). A mineralocorticoid receptor (MR), also known as a type I glucocorticoid receptor (GR I), may be activated by aldosterone in humans. Compositions including modulators of one or both of GR and MR may be used to treat a variety of diseases and disorders. In man, GR may be present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to inhibit the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant (Kd) of $10^{-9}$M (Cadepond (1997) Annu. Rev. Med. 48:129).

In addition to cortisol, the biological effects of other steroids can be modulated at the GR level using receptor modulators, such as agonists, partial agonists and antagonists. When administered to subjects in need thereof, steroids can provide both intended therapeutic effects as well as negative side effects.

Hepatic steatosis, also referred to as fatty liver disease, is a cellular pathology that manifests in the intracellular accumulation of triglycerides and lipids by hepatocytes. Hepatic steatosis is a prevalent liver condition that may arise from a number of etiologies. Such liver disorders include fatty liver disease, nonalcoholic fatty liver disease (NAFLD), nonalcoholic steatohepatitis (NASH), alcohol-induced fatty liver disease (AFLD), drug- or alcohol-related liver diseases, viral diseases, immune-mediated liver diseases, metabolic liver diseases, and complications associated with hepatic insufficiency and/or liver transplantation. Nonalcoholic fatty liver disease is a common hepatic disorder with histological features similar to those of alcohol-induced fatty liver disease, in individuals who consume little or no alcohol. Effective treatments for hepatic steatosis remain insufficient. To date, no therapeutic drug treatment is established for such patients. Thus, there is a need for novel therapeutic options for managing hepatic steatosis.

Administration of antipsychotic medication is an important treatment for many psychiatric disorders, and provides significant relief to the nearly 20 million patients suffering from such disorders. Unfortunately, antipsychotic medications such as olanzapine, risperidine, clozapine, quetiapine, sertindole, and other such medications, often lead to significant weight gain as well as alleviating psychotic symptoms. Numerous reports indicate that about 40-80% of patients who receive antipsychotic medications for long periods of time experience substantial weight gain, ultimately exceeding their ideal body weight by 20% or more (see, e.g., Umbricht et al., J Clin. Psychiatry 55 (Suppl. B):157-160, 1994; Baptista, Acta Psychiatr. Scand. 100:3-16, 1999). Such weight gain increases the risk of many serious health problems associated with obesity, such as cardiovascular disease, stroke, hypertension, type II diabetes, and certain types of cancer. In addition, unwanted weight gain is one of the most common reasons for a patient's non-compliance with the administration of antipsychotic medications.

Over-use of substances such as alcohol, drugs of abuse, cigarettes, and others is a serious problem which often leads to health problems, disease and possibly death. In addition to the medical problems associated with such over-use, other problems occur, including psychological problems, problems in the families of those who over-use such substances, problems in the workplace, and problems in society at large.

The compounds of U.S. Pat. No. 8,685,973 have demonstrated utility for treating one or more of these conditions. What is needed are new forms of these compositions. Surprisingly, the present invention meets these and other needs.

BRIEF SUMMARY OF THE INVENTION

In one embodiment, the present invention provides a composition comprising:

Compound I, (E)-6-(4-Phenylcyclohexyl)-5-(3-trifluoromethylbenzyl)-1H-pyrimidine-2,4-dione:

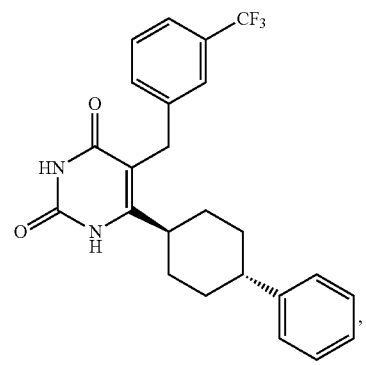 [SMILES: O=c1[nH]c(=O)c(Cc2cccc(C(F)(F)F)c2)c([C@H]2CC[C@H](c3ccccc3)CC2)[nH]1]

in an amount from 15.0 to 32.0% (w/w);
a poly[(methyl methacrylate)-co-(methacrylic acid)] in an amount from 15.0 to 32.0% (w/w);
a sustaining polymer in an amount from 10.0 to 32.0% (w/w);
microcrystalline cellulose in an amount from 10.0 to 25.0% (w/w); and
croscarmellose sodium (Ac-Di-Sol) in an amount from 5.0 to 11.0% (w/w).

In another embodiment, the present invention provides a method of preparing a composition of the present invention, including:

a) forming a mixture comprising a solvent, poly[(methyl methacrylate)-co-(methacrylic acid)], and Compound I, (E)-6-(4-Phenylcyclohexyl)-5-(3-trifluoromethylbenzyl)-1H-pyrimidine-2,4-dione:

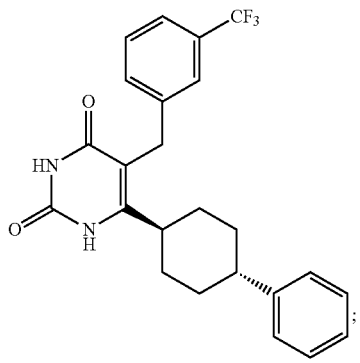 [SMILES: O=c1[nH]c(=O)c(Cc2cccc(C(F)(F)F)c2)c([C@H]2CC[C@H](c3ccccc3)CC2)[nH]1]

b) spray-drying the mixture to form an intermediate mixture;
c) blending a first intragranular mixture comprising the intermediate mixture, a sustaining polymer, microcrystalline cellulose, and croscarmellose sodium;
d) roller compacting the first intragranular mixture to form a roller compacted mixture; and
e) blending a first extragranular mixture comprising the roller compacted mixture and croscarmellose sodium, thereby preparing the composition.

In another embodiment, the present invention provides a method of treating a disorder or condition through modulating a glucocorticoid receptor, comprising administering to a subject in need of such treatment, a therapeutically effective amount of a composition of the present invention, thereby treating the disorder or condition.

In another embodiment, the present invention provides a method of treating a disorder or condition through antagonizing a glucocorticoid receptor, comprising administering to a subject in need of such treatment, a therapeutically effective amount of a composition of the present invention, thereby treating the disorder or condition.

In another embodiment, the present invention provides a method of treating fatty liver disease, comprising administering to a subject in need thereof, a therapeutically effective amount of a composition of the present invention, thereby treating fatty liver disease.

In another embodiment, the present invention provides a method of treating antipsychotic induced weight gain, comprising administering to a subject in need thereof, a therapeutically effective amount of a composition of the present invention, thereby treating antipsychotic induced weight gain.

BRIEF DESCRIPTION OF THE DRAWINGS

FIG. 2 shows the XRPD peaks for Compound I Form B.

FIG. 6 shows a table of PK data for compositions D3 and E1 against C1.
FIG. 7 shows a table of PK data for compositions C1, D1 and D2.

DETAILED DESCRIPTION OF THE INVENTION

I. General

Figure 1:
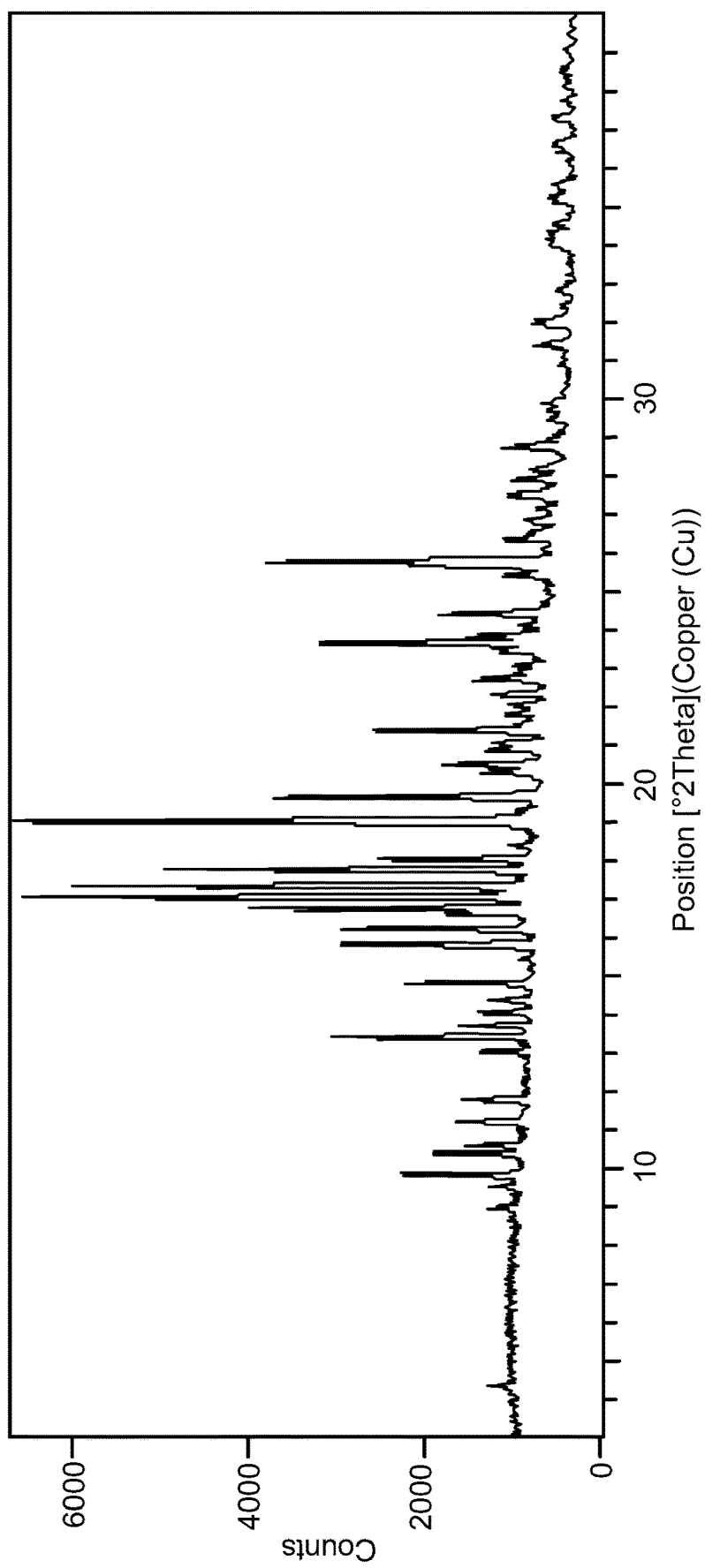
FIG. 1 shows the XRPD pattern for Compound I Form B.

Disclosed herein are formulations of (E)-6-(4-Phenylcyclohexyl)-5-(3-trifluoromethylbenzyl)-1H-pyrimidine-2,4-dione (Compound I):

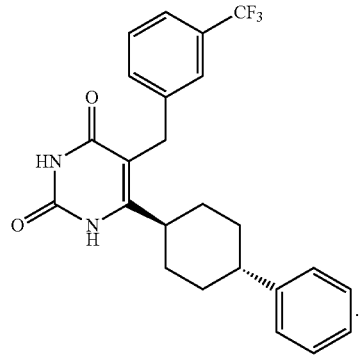 [SMILES: O=c1[nH]c(=O)c(Cc2cccc(C(F)(F)F)c2)c([C@H]2CC[C@H](c3ccccc3)CC2)[nH]1]

II. Definitions

"About" refers to plus or minus 5% of the specified value unless otherwise indicated.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier(s), diluent(s) or excipient(s) must be compatible with the other ingredients of the formulation and not deleterious to the recipient thereof.

"Sustaining polymer" refers to a polymer capable of enhancing the dissolved concentration of an active agent in an in vivo or in vitro environment relative to a comparative composition that does not include the sustaining polymer, and maintains the greater dissolved concentration for an extended period of time.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration to the subject.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR, or both. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR, or both. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An inhibitor is a compound with an $IC_{50}$ (half maximal inhibition concentration) of less than 10 micromolar. See Example 1 of U.S. Pat. No. 8,685,973, the entire contents of which is hereby incorporated by reference in its entirety.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize" and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulators of the present invention. In some embodiments, examples of disorders or conditions include, but are not limited to, obesity, hypertension, depression, anxiety, and Cushing's Syndrome.

"Fatty liver disease" refers to a disease or a pathological condition caused by, at least in part, abnormal hepatic lipid deposits. Fatty liver disease includes, e.g., alcoholic fatty liver disease, nonalcoholic fatty liver disease, and acute fatty liver of pregnancy. Fatty liver disease may be, e.g., macrovesicular steatosis or microvesicular steatosis.

"Non-alcoholic fatty liver disease" ("NAFLD") refers to one of the types of fatty liver which occurs when fat is deposited (steatosis) in the liver due to causes other than excessive alcohol use. NAFLD is considered to cover a spectrum of disease activity. This spectrum begins as fatty accumulation in the liver (hepatic steatosis). Most people with NAFLD have few or no symptoms. Patients may complain of fatigue, malaise, and dull right-upper-quadrant abdominal discomfort. Mild jaundice may be noticed, although this is rare. More commonly NAFLD is diagnosed following abnormal liver function tests during routine blood tests. By definition, alcohol consumption of over 20 g/day (about 25 ml/day of net ethanol) excludes the condition.

"Non-alcoholic steatohepatitis" ("NASH") refers to the most extreme form of NAFLD. NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

"Substance use disorder" refers to the compulsive use of a substance despite unpleasant or harmful consequences of that use. A substance use disorder may involve impaired control (e.g., use of excessive amounts of the substance, or over longer periods of time, than was originally intended), social impairment (e.g., failure to fulfill major roles obligations at work, school, or home), risky use (e.g., recurrent use of the substance in situations in which it is physically hazardous), and pharmacological criteria (e.g., tolerance or withdrawal). A substance use disorder may have formerly been termed an "addiction" although, since the publication of the *Diagnostic and Statistical Manual of Mental Disorders Fifth Edition DSM*-5 (hereafter "DSM-V"), terms such as "addiction" and "addict" have been replaced for the terms "substance use disorder" (replacing "addiction") and person suffering from a substance use disorder (replacing "addict"). A person suffering from a substance use disorder may be termed as suffering from a substance use disorder related to a particular substance; prior to the publication of DSM-V, such a person may have been described as being "addicted to" that substance. For example, where a person has a substance use disorder related to a stimulant, that person may have been described as being "addicted to" that stimulant prior to the publication of DSM-V.

"Substance" as recited in phrases such as "substance use disorder related to said substance" and "substance use disorder related to the substance" refers to the substance for which a patient has a craving, or which the patient uses compulsively despite unpleasant or harmful consequences of that use. Thus, such a "substance" is the substance used by, or ingested, or otherwise administered to (including self-administration) a person who suffers from a substance use disorder related to that substance. The terms "substance of addiction", and "substance of abuse" may have formerly been used to refer such a substance, which substance may formerly have been termed an "addictive substance" (e.g., prior to the publication of DSM-V).

"Person suffering from a substance use disorder" refers to a person suffering from a substance use disorder related to a particular substance, or, in some cases, more than one particular substance. Such a "substance" may be a drug, or alcohol, or a cigarette, or other substance a person may take (ingest). For example, such a "substance" may be alcohol, a stimulant, an opioid, or other substance.

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

III. Compositions

The present invention provides pharmaceutically acceptable compositions of (E)-6-(4-Phenylcyclohexyl)-5-(3-trifluoromethylbenzyl)-1H-pyrimidine-2,4-dione (Compound I; see U.S. Pat. No. 8,685,973) which provide surprisingly improved bioavailability of Compound I. Compound I is difficult to solubilize in a forms suitable for use in pharmaceutical compositions; routine methods have proven unsuccessful in providing pharmaceutically acceptable compositions of this compound. Surprisingly, the compositions disclosed herein overcome the previously problems of solubility and bioavailability, and provide pharmaceutically acceptable compositions with enhanced bioavailability, suitable for use in treating conditions and disorders amenable to treatment by administration of Compound I.

The present invention provides compositions of (E)-6-(4-Phenylcyclohexyl)-5-(3-trifluoromethylbenzyl)-1H-pyrimidine-2,4-dione (Compound I; CORT118335; miricorilant; see U.S. Pat. No. 8,685,973). In some embodiments, the present invention provides a composition including Compound I having the structure:

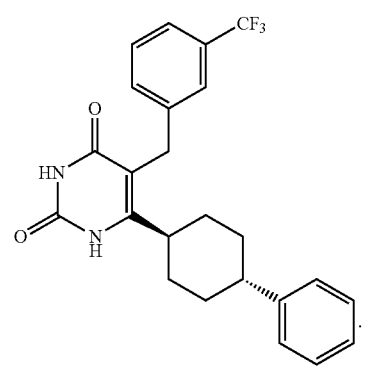 [SMILES: O=c1[nH]c(=O)c(Cc2cccc(C(F)(F)F)c2)c([C@H]2CC[C@H](c3ccccc3)CC2)[nH]1]

The compound can also be named 6-(trans-4-phenylcyclohexyl)-5-(3-(trifluoromethyl)phenyl)methyl)pyrimidine-2,4(1H,3H)-dione or 6-((1r,4)-4-phenylcyclohexyl)-5-(3-(trifluoromethyl)benzyl)pyrimidine-2,4(1H,3H)-dione.

In some embodiments, the present invention provides a composition comprising:

Compound I, (E)-6-(4-Phenylcyclohexyl)-5-(3-trifluoromethylbenzyl)-1H-pyrimidine-2,4-dione:

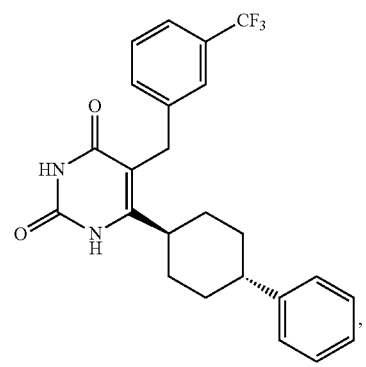 [SMILES: O=c1[nH]c(=O)c(Cc2cccc(C(F)(F)F)c2)c([C@H]2CC[C@H](c3ccccc3)CC2)[nH]1]

in an amount from 15.0 to 32.0% (w/w);
a poly[(methyl methacrylate)-co-(methacrylic acid)] in an amount from 15.0 to 32.0% (w/w);
a sustaining polymer in an amount from 10.0 to 32.0% (w/w);
microcrystalline cellulose in an amount from 10.0 to 25.0% (w/w); and
croscarmellose sodium (Ac-Di-Sol) in an amount from 5.0 to 11.0% (w/w).

Compound I can be present in the composition in any suitable amount. Representative amounts of Compound I include, but are not limited to, about 10 mg, or 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or about 500 mg. In some embodiment, the composition includes Compound I in an amount of about 150 mg.

Compound I can be present in the composition in any suitable weight percentage. Representative amounts of Compound I in the composition include, but are not limited to, 1 to 50% (w/w), or 5 to 45%, or 5 to 40%, or 10 to 35%, or 15 to 32%, or 16 to 31%, or 17 to 30%, or 18 to 29%, or 20 to 28%, or 21 to 27%, or 22 to 26%, or 23 to 25% (w/w). Other amount of Compound I in the composition include, but are not limited to, about 15% (w/w), or about 16, 17, 18, 19, 20, 21, 22, 23, 24, 25, 26, 27, 28, 29, 30, 31, 32, 33, 34, or about 35% (w/w). In some embodiments, Compound I is present in an amount of from 20.0 to 28.0% (w/w). In some embodiments, Compound I is present in an amount of from 22.0 to 28.0% (w/w). In some embodiments, Compound I is present in an amount of about 22.8% (w/w). In some embodiments, Compound I is present in an amount of about 22.9% (w/w). In some embodiments, Compound I is present in an amount of about 25.0% (w/w). In some embodiments, Compound I is present in an amount of about 26.1% (w/w). In some embodiments, Compound I is present in an amount of about 27.3% (w/w). In some embodiments, Compound I is present in an amount of about 30.0% (w/w).

In some embodiments, the composition includes
Compound I is present in an amount from 20.0 to 28.0% (w/w);
a polymer in an amount from 20.0 to 28.0% (w/w); and
a sustaining polymer in an amount from 10.0 to 28.0% (w/w).

The composition can also include one or more polymers. Representative polymers include, but are not limited to, polyacrylates, polymethyacrylates, poly(methyl methacrylate), poly(methacrylic acid), cellulose, etc. The polymer can include homopolymers and copolymers. The copolymers can include block copolymers, random copolymers, etc. The monomers of the copolymer can be present in any suitable molar ratio, such as from 10:1 to 1:10. For example, the polymer can include poly[(methyl methacrylate)-co-(methacrylic acid)].

In some embodiments, the composition includes
Compound I is present in an amount from 20.0 to 28.0% (w/w);
a poly[(methyl methacrylate)-co-(methacrylic acid)] in an amount from 20.0 to 28.0% (w/w); and
a sustaining polymer in an amount from 10.0 to 28.0% (w/w).

In some embodiments, the poly[(methyl methacrylate)-co-(methacrylic acid)] is Eudragit L100.

The poly[(methyl methacrylate)-co-(methacrylic acid)] can be present in any suitable ratio to Compound I. For example, the weight ratio of Compound I to the poly[(methyl methacrylate)-co-(methacrylic acid)] can be from 5:1 to 1:5, or 4:1 to 1:2, 3:1 to 1:2, 2:1 to 1:1.5, or 1.5:1 to 1:1.5. In some embodiments, the weight ratio of Compound I to the poly[(methyl methacrylate)-co-(methacrylic acid)] is about 1:1.

The poly[(methyl methacrylate)-co-(methacrylic acid)] can be present in the composition in any suitable weight percentage. Representative amounts of the poly[(methyl methacrylate)-co-(methacrylic acid)] in the composition include, but are not limited to, 1 to 50% (w/w), or 5 to 45%, or 5 to 40%, or 10 to 35%, or 15 to 32%, or 16 to 31%, or 17 to 30%, or 18 to 29%, or 20 to 28%, or 21 to 27%, or 22 to 26%, or 23 to 25% (w/w). Other amount of the poly[(methyl methacrylate)-co-(methacrylic acid)] in the composition include, but are not limited to, about 15% (w/w), or about 16, 17, 18, 19, 20, 21, 22, 23, 24, 25, 26, 27, 28, 29, 30, 31, 32, 33, 34, or about 35% (w/w). In some embodiments, the poly[(methyl methacrylate)-co-(methacrylic acid)] is present in an amount of from 20.0 to 28.0% (w/w). In some embodiments, the poly[(methyl methacrylate)-co-(methacrylic acid)] is present in an amount of from 22.0 to 28.0% (w/w). In some embodiments, the poly[(methyl methacrylate)-co-(methacrylic acid)] is present in an amount of about 22.8% (w/w). In some embodiments, the poly[(methyl methacrylate)-co-(methacrylic acid)] is present in an amount of about 22.9% (w/w). In some embodiments, the poly[(methyl methacrylate)-co-(methacrylic acid)] is present in an amount of about 25.0% (w/w). In some embodiments, the poly[(methyl methacrylate)-co-(methacrylic acid)] is present in an amount of about 26.1% (w/w). In some embodiments, the poly[(methyl methacrylate)-co-(methacrylic acid)] is present in an amount of about 27.3% (w/w). In some embodiments, the poly[(methyl methacrylate)-co-(methacrylic acid)] is present in an amount of about 30.0% (w/w).

The compositions of the present invention can also include a sustaining polymer. For example, the sustaining polymer can include, but is not limited to, an ionizable cellulosic polymer, a non-ionizable cellulosic polymer, an ionizable non-cellulosic polymer, a non-ionizable non-cellulosic polymer, or a combination thereof.

Ionizable cellulosic polymers include hydroxypropyl methyl cellulose succinate, cellulose acetate succinate, methyl cellulose acetate succinate, ethyl cellulose acetate succinate, hydroxypropyl cellulose acetate succinate, hydroxypropyl methyl cellulose acetate succinate, hydroxypropyl cellulose acetate phthalate succinate, cellulose propionate succinate, hydroxypropyl cellulose butyrate succinate, hydroxypropyl methyl cellulose phthalate, cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxy methyl cellulose, carboxy ethyl cellulose, ethyl carboxy methyl cellulose, and combinations thereof.

Non-ionizable cellulosic polymers include hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose, and combinations thereof.

Ionizable non-cellulosic polymers include carboxylic acid functionalized polymethacrylates, carboxylic acid functionalized polyacrylates, amine-functionalized polyacrylates, amine-functionalized polymethacrylates, proteins, and carboxylic acid functionalized starches, and combinations thereof.

Non-ionizable non-cellulosic polymers include vinyl polymers and copolymers having at least one substituent selected from the group consisting of hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed form, polyvinyl alcohol polyvinyl acetate copolymers, polyethylene glycol polypropylene glycol copolymers, polyvinyl pyrrolidone, and polyethylene polyvinyl alcohol copolymers, and combinations thereof.

In some embodiments, the sustaining polymer comprises hydroxypropyl methylcellulose acetate succinate (HPMCAS), hydroxypropyl methylcellulose (HPMC), poly(vinylpyrrolidone-co-vinyl acetate) (PVPVA), carboxymethyl ethylcellulose (CMEC), or a combination thereof. In some embodiments, the sustaining polymer comprises HPMCAS or PVPVA. The HPMCAS may be, for example, HPMCAS-HF (also HPMCAS-H) or Affinisol® 126 HPMCAS polymer (The Dow Chemical Company). HPMCAS-HF has an average particle size of <10 pm, such as an average particle size of 5 pm, as measured by laser diffraction. HPMCAS-HF and Affinisol® 126 HPMCAS each have an acetyl content of 10-14 wt %, a succinoyl content of 4-8 wt %, a methoxy content of 22-26 wt %, and a hydroxypropoxy content of 6-10 wt %. HPCMAS-HF and Affinisol® 126 HPMCAS have an acid content of 0.7 mmol acid/gram and are soluble at pH>6.5. The PVPVA may be, for example, PVPVA64—a linear random copolymer with a 6:4 ratio of /V-vinylpyrrolidone and vinyl acetate. One commercially available example is Kollidon® VA 64 polymer (BASF Corporation). In some embodiments, the sustaining polymer comprises PVPVA.

In some embodiments, the sustaining polymer is hydroxypropyl methylcellulose acetate succinate (HPMCAS). Hydroxypropyl methylcellulose acetate succinate (HPMCAS) can be in one of several different grades including, but not limited to, high fine grade (HPMCAS-H or HPMCAS-HF), medium grade (HPMCAS-M), and low grade (HPMCAS-L). In some embodiments, the sustaining polymer is hydroxypropyl methylcellulose acetate succinate high fine grade (HPMCAS-H).

The sustaining polymer can be present in any suitable ratio to Compound I. For example, the weight ratio of Compound I to the sustaining polymer can be from 5:1 to 1:5, or 4:1 to 1:2, 3:1 to 1:2, 2:1 to 1:1.5, or 1.5:1 to 1:1.5. In some embodiments, the weight ratio of Compound I to the sustaining polymer is about 2:1. In some embodiments, the weight ratio of Compound I to the sustaining polymer is about 1.3:1. In some embodiments, the weight ratio of Compound I to the sustaining polymer is about 1:1. In some embodiments, the weight ratio of Compound I to the HPMCAS-H is about 1:1.

The sustaining polymer can be present in the composition in any suitable weight percentage. Representative amounts of the sustaining polymer in the composition include, but are not limited to, 1 to 50% (w/w), or 5 to 45%, or 5 to 40%, or 10 to 35%, or 10 to 30%, or 13 to 28% (w/w). Other amounts of the sustaining polymer in the composition include, but are not limited to, about 10% (w/w), or about 11, 12, 13, 14, 15, 16, 17, 18, 19, 20, 21, 22, 23, 24, 25, 26, 27, 28, 29, or about 30% (w/w). In some embodiments, the sustaining polymer is present in an amount of from 13.0 to 28.0% (w/w). In some embodiments, the sustaining polymer is present in an amount of about 14.0% (w/w). In some embodiments, the sustaining polymer is present in an amount of about 20.5% (w/w). In some embodiments, the sustaining polymer is present in an amount of about 22.9% (w/w). In some embodiments, the sustaining polymer is present in an amount of about 23.0% (w/w). In some embodiments, the sustaining polymer is present in an amount of about 25.0% (w/w). In some embodiments, the sustaining polymer is present in an amount of about 26.1% (w/w).

The compositions of the present invention can also include at least one filler in any suitable amount. Representative fillers include, but are not limited to, starch, lactitol, lactose, an inorganic calcium salt, microcrystalline cellulose, sucrose, and combinations thereof. In some embodiments, the filler includes microcrystalline cellulose. In some embodiments, the filler includes microcrystalline cellulose (Avicel PH102). In some embodiments, the filler includes microcrystalline cellulose (Avicel PH101).

The compositions of the present invention can also include at least one disintegrant in any suitable amount. Representative disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums (like gellan), low-substituted hydroxypropyl cellulose, or mixtures thereof. In some embodiments, the disintegrant includes croscarmellose sodium. In some embodiments, the disintegrant includes croscarmellose sodium (Ac-Di-Sol).

In some embodiments, the composition includes:
Compound I, in an amount from 22.0 to 28.0% (w/w);
Eudragit L100 in an amount from 22.0 to 28.0% (w/w);
hydroxypropyl methylcellulose acetate succinate high fine grade in an amount from 13.0 to 28.0% (w/w);
microcrystalline cellulose (Avicel PH102) in an amount from 13.0 to 20.0% (w/w); and
croscarmellose sodium (Ac-Di-Sol) in an amount from 5.0 to 11.0% (w/w).

The compositions of the present invention can also include sodium lauryl sulfate in any suitable amount. Representative amounts of the sodium lauryl sulfate in the composition include, but are not limited to, from 0.1 to 10% (w/w), or 0.2 to 9%, or 0.3 to 8%, or 0.4 to 7%, or 0.4 to 6%, or 0.5 to 5%, or 1 to 5%, or 1 to 4%, or 1 to 3% or 1 to 2%, or 1.0 to 1.9%, or 1.2 to 1.8%, or 1.25 to 1.75%, or from 1.3 to 1.5% (w/w). Other amounts of the sodium lauryl sulfate in the composition include, but are not limited to, about 1.0% (w/w), or about 1.1, 1.2, 1.3, 1.4, 1.5, 1.6, 1.7, 1.8, 1.9, or about 2.0% (w/w). In some embodiments, the composition includes sodium lauryl sulfate in an amount from 0.5 to 5.0% (w/w). In some embodiments, the composition includes sodium lauryl sulfate in an amount from 1.25 to 1.75% (w/w). In some embodiments, the composition includes sodium lauryl sulfate in an amount from 1.3 to 1.5% (w/w). In some embodiments, the composition includes sodium lauryl sulfate in an amount from 1.4% (w/w).

The compositions of the present invention can also include a lubricant. Representative lubricants include, but are not limited to, calcium stearate, magnesium stearate, mineral oil, light mineral oil, glycerin, sorbitol, mannitol, polyethylene glycol, other glycols, stearic acid, sodium lauryl sulfate, sodium stearyl fumarate, vegetable based fatty acids lubricant, hydrogenated vegetable oil (e.g., peanut oil, cottonseed oil, sunflower oil, sesame oil, olive oil, corn oil and soybean oil), zinc stearate, ethyl oleate, ethyl laurate, agar, or mixtures thereof. In some embodiments, the lubricant includes magnesium stearate.

In some embodiments, the composition includes:
Compound I, in an amount of about 22.8% (w/w);
Eudragit L100 in an amount of about 22.8% (w/w);
sodium lauryl sulfate in an amount of about 1.4% (w/w);
hydroxypropyl methylcellulose acetate succinate high fine grade in an amount of about 23.0% (w/w);

microcrystalline cellulose (Avicel PH102) in an amount of about 19.4% (w/w);
croscarmellose sodium (Ac-Di-Sol) in an amount of about 10.0% (w/w); and
magnesium stearate in an amount of about 0.5% (w/w).

In some embodiments, the composition can be a tablet. The tablet compositions can be of any suitable size such as, but not limited to, 25, 50, 75, 100, 110, 120, 130, 140, 150, 160, 170, 180, 190, 200, 250, 300, 350, 400, 450, 500, 550, 600, 650, 700, 750, 800, 850, 900, 950, or 1000 mg tablets. In some embodiments, the composition is a 650 mg tablet.

In some embodiments, the composition includes:
Compound I, in an amount of about 150 mg;
Eudragit L100 in an amount of about 150 mg;
sodium lauryl sulfate in an amount of about 9.3 mg;
hydroxypropyl methylcellulose acetate succinate high fine grade in an amount of about 152 mg;
microcrystalline cellulose (Avicel PH102) in an amount of about 128.1 mg;
croscarmellose sodium (Ac-Di-Sol) in an amount of about 66 mg; and
magnesium stearate in an amount of about 3.3 mg.

The compositions of the present invention can also include at least one glidant in any suitable amount. In some embodiments, the composition includes talc and colloidal silicon dioxide. In some embodiments, the composition includes colloidal silicon dioxide (Cab-O-Sil MP5). In some embodiments, the composition includes colloidal silicon dioxide (Cab-O-Sil MP5) in an amount from 0.1 to 2.0% (w/w). In some embodiments, the composition includes colloidal silicon dioxide (Cab-O-Sil MP5) in an amount from 0.1 to 1.5% (w/w). In some embodiments, the composition includes colloidal silicon dioxide (Cab-O-Sil MP5) in an amount from 0.5 to 2.0% (w/w). In some embodiments, the composition includes colloidal silicon dioxide (Cab-O-Sil MP5) in an amount from 0.50 to 1.5% (w/w).

In some embodiments, the composition includes:
Compound I, in an amount of about 22.8% (w/w);
Eudragit L100 in an amount of about 22.8% (w/w);
sodium lauryl sulfate in an amount of about 1.4% (w/w);
hydroxypropyl methylcellulose acetate succinate high fine grade in an amount of about 23.0% (w/w);
microcrystalline cellulose (Avicel PH102) in an amount of about 18.4% (w/w);
croscarmellose sodium (Ac-Di-Sol) in an amount of about 10.0% (w/w);
colloidal silicon dioxide (Cab-O-Sil MP5) in an amount of about 1.0% (w/w); and
magnesium stearate in an amount of about 0.5% (w/w).

In some embodiments, the composition includes:
Compound I, in an amount of about 150 mg;
Eudragit L100 in an amount of about 150 mg;
sodium lauryl sulfate in an amount of about 9.3 mg;
hydroxypropyl methylcellulose acetate succinate high fine grade in an amount of about 150.9 mg;
microcrystalline cellulose (Avicel PH102) in an amount of about 120.7 mg;
croscarmellose sodium (Ac-Di-Sol) in an amount of about 65.6 mg;
colloidal silicon dioxide (Cab-O-Sil MP5) in an amount of about 6.6 mg; and
magnesium stearate in an amount of about 3.3 mg.

The compositions of the present invention can also include at least one filler in any suitable amount. Representative fillers include, but are not limited to, talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & amp; guar gum, molasses, sucrose, or mixtures thereof. In some embodiments, the composition include microcrystalline cellulose. In some embodiments, the composition includes microcrystalline cellulose (Avicel PH102) in an amount from 10.0 to 30.0% (w/w). In some embodiments, the composition includes microcrystalline cellulose (Avicel PH102) in an amount from 13.0 to 20.0% (w/w).

In some embodiments, the composition includes:
Compound I, in an amount of about 25.0% (w/w);
Eudragit L100 in an amount of about 25.0% (w/w);
hydroxypropyl methylcellulose acetate succinate high fine grade in an amount of about 25.0% (w/w);
microcrystalline cellulose (Avicel PH102) in an amount of about 13.75% (w/w);
croscarmellose sodium (Ac-Di-Sol) in an amount of about 10.0% (w/w);
colloidal silicon dioxide (Cab-O-Sil MP5) in an amount of about 0.75% (w/w); and
magnesium stearate in an amount of about 0.5% (w/w).

In some embodiments, the composition includes:
Compound I, in an amount of about 22.9% (w/w);
Eudragit L100 in an amount of about 22.9% (w/w);
hydroxypropyl methylcellulose acetate succinate high fine grade in an amount of about 22.9% (w/w);
microcrystalline cellulose (Avicel PH102) in an amount of about 19.8% (w/w);
croscarmellose sodium (Ac-Di-Sol) in an amount of about 10.0% (w/w);
colloidal silicon dioxide (Cab-O-Sil MP5) in an amount of about 1.0% (w/w); and
magnesium stearate in an amount of about 0.5% (w/w).

The compositions of the present invention can be prepared and administered in a wide variety of oral dosage forms. Oral preparations include tablets, pills, powder, dragees, capsules, slurries, suspensions, etc., suitable for ingestion by the patient. Accordingly, the present invention also provides pharmaceutical compositions including one or more pharmaceutically acceptable carriers and/or excipients and either a compound, or a pharmaceutically acceptable salt of a compound.

For preparing compositions from Compound I, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfactants, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excipients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain The compositions mixed with a filler or binders such as lactose or starches, lubricants such as talc or magnesium stearate, and, optionally, stabilizers. In soft capsules, The compositions may be dissolved or suspended in suitable liquids, such as fatty oils, liquid paraffin, or liquid polyethylene glycol with or without stabilizers.

Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

The pharmaceutical preparation can be prepared in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, 1.0 mg to 1000 mg, or 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR and/or MR modulator and disease or condition treated.

Single or multiple administrations of the compositions can be administered depending on the dosage and frequency as required and tolerated by the patient. The compounds should provide a sufficient quantity of active agent to effectively treat the disease state. Thus, in some embodiments, the pharmaceutical formulations for oral administration of the compound is in a daily amount of between about 0.5 to about 30 mg per kilogram of body weight per day. In some embodiments, dosages can be from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

Compound I described herein can be used in combination with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including a compound of the invention has been formulated in one or more acceptable carriers, it can be placed in an appropriate container and labeled for treatment of an indicated condition. For administration of Compound I, such labeling would include, e.g., instructions concerning the amount, frequency and method of administration.

IV. Method of Making Formulations

The compositions of the present invention can be prepared by a variety of methods. In some embodiments, the present invention provides a method of preparing a composition of the present invention, including:

a) forming a mixture comprising a solvent, poly[(methyl methacrylate)-co-(methacrylic acid)], and Compound I, (E)-6-(4-Phenylcyclohexyl)-5-(3-trifluoromethyl-benzyl)-1H-pyrimidine-2,4-dione:

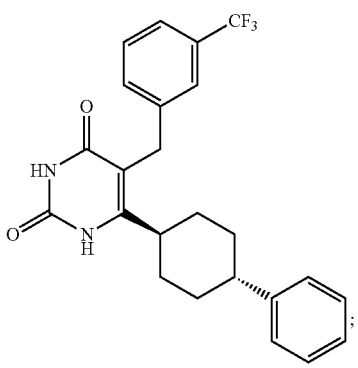 [SMILES: O=c1[nH]c(=O)c(Cc2cccc(C(F)(F)F)c2)c([C@H]2CC[C@H](c3ccccc3)CC2)[nH]1]

b) spray-drying the mixture to form an intermediate mixture;
c) blending a first intragranular mixture comprising the intermediate mixture, a sustaining polymer, microcrystalline cellulose, and croscarmellose sodium;
d) roller compacting the first intragranular mixture to form a roller compacted mixture; and
e) blending a first extragranular mixture comprising the roller compacted mixture and croscarmellose sodium, thereby preparing the composition.

The mixture can include any suitable solvent or combination of solvents. Suitable solvents include, but are not limited to, petroleum ether, $C_1$-$C_3$ alcohols (methanol, ethanol, propanol, isopropanol), ethylene glycol and polyethylene glycol such as PEG400, alkanoates such as ethyl acetate, propyl acetate, isopropyl acetate, and butyl acetate, acetonitrile, alkanones such as acetone, butanone, methyl ethyl ketone (MEK), methyl propyl ketone (MPK) and methyl iso-butyl ketone (MIBK), ethers such as diethyl ether, methyl-t-butyl ether, tetrahydrofuran, methyl-tetrahydrofuran, 1,2-dimethoxy ethane and 1,4-dioxane, halogenated solvents such as methylene chloride, chloroform and carbon tetrachloride, dimethylsulfoxide (DMSO), and dimethylformamide (DMF). Suitable solvents also include, but are not limited to halogenated $C_1$-$C_3$ alcohols (trifluoromethanol, trifluoroethanol (TFE), hexafluoroisopropanol (HFIPA)). For example, the solvent can be a polar aprotic solvent such as dichloromethane, N-methylpyrrolidone, tetrahydrofuran, ethyl acetate, acetone, methyl ethyl ketone, dimethylformamide (DMF), acetonitrile (AcCN), dimethyl sulfoxide (DMSO), among others. The solvent can also be a polar protic solvent such as t-butanol, n-propanol, isopropanol, ethanol, methanol, acetic acid, among others. The solvent can also be a non-polar solvent, such as, diethyl ether, methyl-t-butyl ether, tetrahydrofuran, methyl-tetrahydrofuran, 1,2-dimethoxy ethane and 1,4-dioxane, chloroform, and carbon tetrachloride.

Two or more solvents can be used in a solvent mixture in any suitable ratio. For example, the ratio of a first solvent and a second solvent can be from 10:1 to about 1:10 (volume/volume or weight/weight), or about 10:1 to 1:5, or 10:1 to 1:1, or 10:1 to 5:1, or 5:1 to 1:5, or 5:1 to 1:1, or 4:1 to 1:1, or 3:1 to 1:1, or 2:1 to 1:1. Other solvent ratios include about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or about 1:10 (volume/volume or weight/weight).

In some embodiments, the solvent includes methanol and dichloromethane. In some embodiments, the solvent includes acetone.

In some embodiments, the poly[(methyl methacrylate)-co-(methacrylic acid)] is Eudragit L100.

The methods can include Compound I in any suitable form. For example, Compound I can be amorphous or crystalline. In some embodiments, Compound I is a crystalline anhydrate. In some embodiments, Compound I is crystalline Form B.

In some embodiments, the methods of the present invention include a crystalline anhydrate form of the Compound I. In some embodiments, the Compound I Form B is characterized by an XRPD pattern comprising peaks at 16.7, 17.0, 17.3, 17.7, 19.0, 19.6, and 23.6° 2θ±0.2° 2θ. In some embodiments, the Compound I Form B is characterized by an XRPD pattern comprising peaks at 9.8, 10.4, 11.2, 11.8, 13.4, 13.7, 14.8, 15.8, 16.2, 16.6, 16.7, 17.0, 17.3, 17.7, 18.0, 19.0, 19.6, 20.3, 20.5, 20.8, 21.0, 21.3, 22.0, 22.3, 22.7, 23.6, 23.8, 24.4, 25.4, 25.6, 25.7, 26.3, 28.1, 28.7, and 37.2° 2θ±0.2° 2θ. In some embodiments, the Compound I Form B is characterized by an XRPD pattern substantially as shown in FIG. 1.

Figure 3:
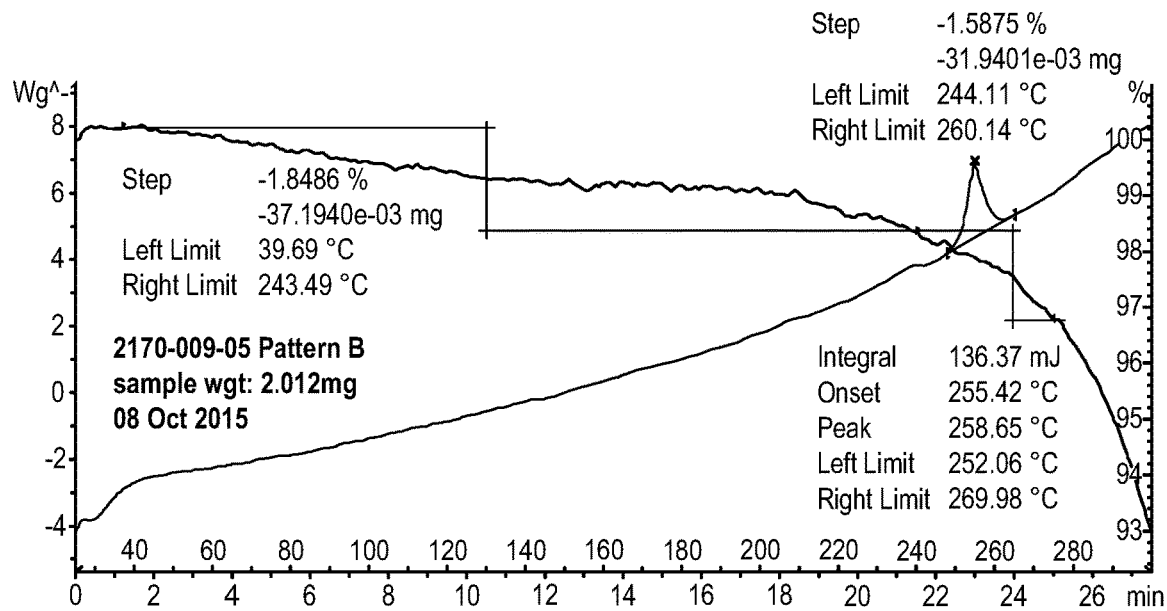
FIG. 3 shows the DSC and TGA thermogram for Compound I Form B.
Figure 4:
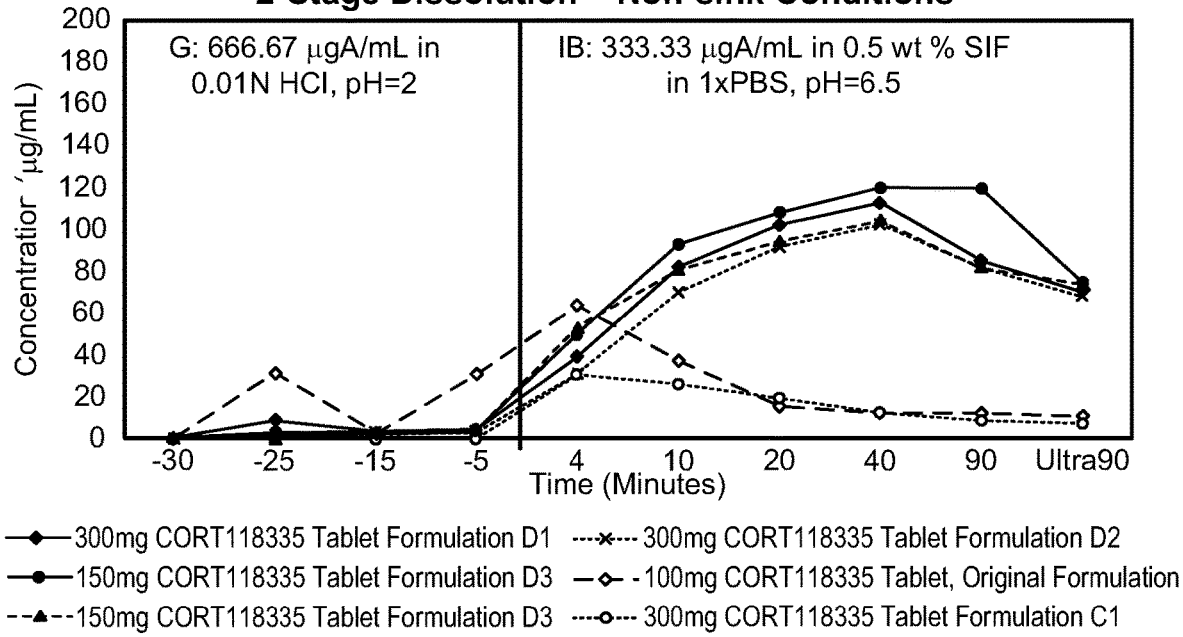
FIG. 4 shows the dissolution graph of formulations D1, D2, D3 and E1 using Compound I (CORT118335).
Figure 5:
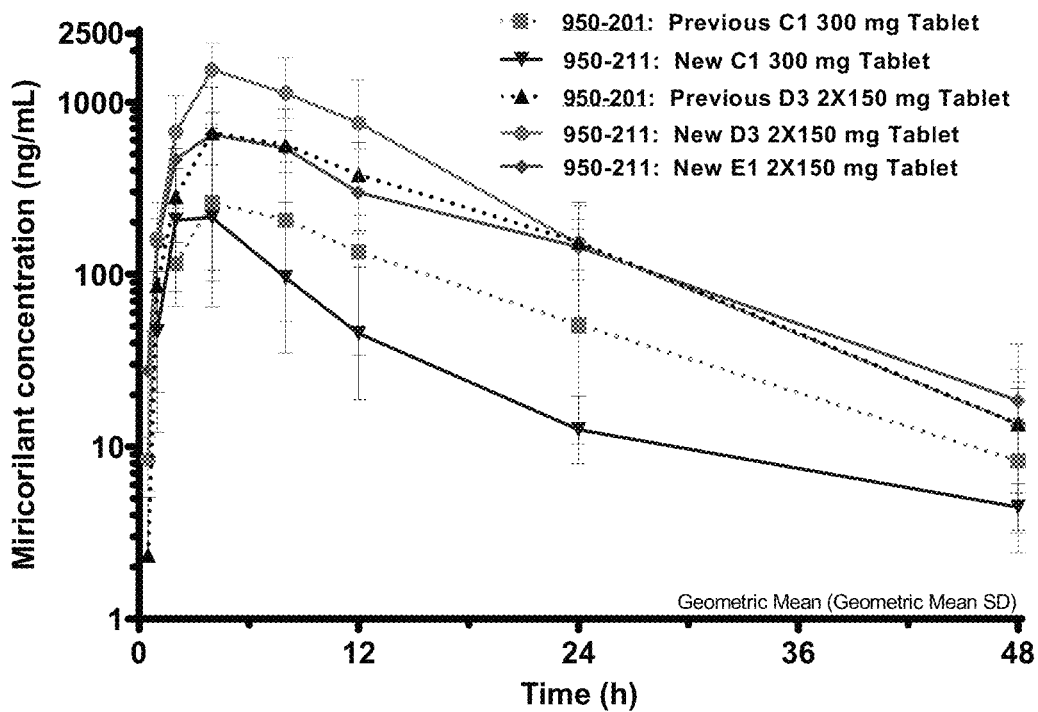
FIG. 5 shows in vivo bioavailability results of Compound I (miricorilant) in monkeys administered tablets prepared according to the C1, D3 and E1 compositions. Tablets prepared with the new formulations performed better than tablets prepared with earlier formulations; the improvement in bioavailability in vivo was several-fold compared with the earlier formulations.

In some embodiments, the Compound I Form B is characterized by a differential scanning calorimetry (DSC) thermogram having at least one endotherm with an onset of about 255° C. In some embodiments, the Compound I Form B is characterized by a DSC thermogram substantially as shown in FIG. 3.

In some embodiments, the Compound I Form B is characterized by: (a) an XRPD pattern comprising peaks at 16.7, 17.0, 17.3, 17.7, 19.0, 19.6, and 23.6° 2θ±0.2° 2θ; and (b) a differential scanning calorimetry (DSC) thermogram having an endotherm with an onset of about 255° C. In some embodiments, the Compound I Form B is characterized by: (a) an XRPD pattern substantially as shown in FIG. 1; and (b) a DSC thermogram substantially as shown in FIG. 3.

The sustaining polymer can be any suitable sustaining polymer as described above. In some embodiments, the sustaining polymer is hydroxypropyl methylcellulose acetate succinate (HPMCAS). In some embodiments, the sustaining polymer is hydroxypropyl methylcellulose acetate succinate high fine grade (HPMCAS-H).

In some embodiments, the method includes:
a) forming the mixture comprising the solvent, Eudragit L100, sodium lauryl sulfate (SLS), and Compound I;
b) spray-drying the mixture to form the intermediate mixture;
c1) blending the first intragranular mixture comprising the intermediate mixture, HPMCAS-H, microcrystalline cellulose, and croscarmellose sodium;
c2) blending a second intragranular mixture comprising the first intragranular mixture and magnesium stearate;
d) roller compacting the second intragranular mixture to form a roller compacted mixture;
e1) blending the first extragranular mixture comprising the roller compacted mixture and croscarmellose sodium; and
e2) blending a second extragranular mixture comprising the first extragranular mixture and magnesium stearate, thereby preparing the composition.

The method can also include any suitable glidant as described above. In some embodiments, the first intragranular mixture further comprises a first glidant; and the first extragranular mixture further comprises a second glidant. In some embodiments, the first glidant and second glidant each comprise colloidal silicon dioxide.

In some embodiments, the method includes:
a) forming the mixture comprising the solvent, Eudragit L100, sodium lauryl sulfate (SLS), and Compound I;
b) spray-drying the mixture to form the intermediate mixture;

c1) blending the first intragranular mixture comprising the intermediate mixture, HPMCAS-H, microcrystalline cellulose, croscarmellose sodium and colloidal silicon dioxide;
c2) blending a second intragranular mixture comprising the first intragranular mixture and magnesium stearate;
d) roller compacting the second intragranular mixture to form a roller compacted mixture;
e1) blending the first extragranular mixture comprising the roller compacted mixture, croscarmellose sodium and colloidal silicon dioxide; and
e2) blending a second extragranular mixture comprising the first extragranular mixture and magnesium stearate, thereby preparing the composition.

In some embodiments, the method includes:
a) forming the mixture comprising the solvent, poly [(methyl methacrylate)-co-(methacrylic acid)], and Compound I;
b) spray-drying the mixture to form the intermediate mixture;
c1) blending the first intragranular mixture comprising the intermediate mixture, HPMCAS-H, microcrystalline cellulose, croscarmellose sodium and colloidal silicon dioxide;
c2) blending a second intragranular mixture comprising the first intragranular mixture and magnesium stearate;
d) roller compacting the second intragranular mixture to form a roller compacted mixture;
e1) blending the first extragranular mixture comprising the roller compacted mixture, croscarmellose sodium and colloidal silicon dioxide; and
e2) blending a second extragranular mixture comprising the first extragranular mixture and magnesium stearate, thereby preparing the composition.

The method can be used to prepare the compositions at any suitable scale, for example, from gram to kilogram. For example, the method can include Compound I in an amount of at least 5 g, 10 g, 15 g, 20 g, 25 g, 30 g, 35 g, 40 g, 45 g, 50 g, 60 g, 70 g, 80 g, 90 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 60 kg, 70 kg, 80 kg, 90 kg, 100 kg, 200 kg, 250 kg, 300 kg, 400 kg, 500 kg, or at least 1000 kg or more.

The temperature of the mixtures and reaction steps can be any suitable temperature, such as from 0° C. to 100° C., or from 20° C. to 50° C.

The method of the present invention can be performed at any suitable pressure. For example, the method can be at atmospheric pressure. The various steps of the methods can also be exposed to any suitable environment, such as atmospheric gases, or inert gases such as nitrogen or argon.

V. Methods of Use

In some embodiments, the present invention provides a method of treating a disorder or condition through modulating a glucocorticoid receptor, comprising administering to a subject in need of such treatment, a therapeutically effective amount of a composition of the present invention, thereby treating the disorder or condition.

In some embodiments, the present invention provides a method of treating a disorder or condition through antagonizing a glucocorticoid receptor, comprising administering to a subject in need of such treatment, a therapeutically effective amount of a composition of the present invention, thereby treating the disorder or condition.

In some embodiments, the present invention provides methods of modulating glucocorticoid receptor activity using the techniques described herein. In some embodiments, the method includes contacting a GR with an effective amount of a composition of the present invention, and detecting a change in GR activity.

In some embodiments, the present invention provides methods of modulating glucocorticoid receptor activity using the techniques described herein. In some embodiments, the method includes contacting a GR or both with an effective amount of a composition of the present invention, and detecting a change in GR activity, MR activity, or both.

In some embodiments, the glucocorticoid receptor modulator is an antagonist of GR activity or MR activity, or both GR and MR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor agonist (e.g. cortisol, aldosterone, and synthetic or natural cortisol or aldosterone analogs) to a GR, thereby inhibiting any biological response associated with the binding of a GR, to the agonist.

In some embodiments, the glucocorticoid receptor modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the androgen receptor (AR), estrogen receptor (ER) or progesterone receptor (PR). In some embodiments, the specific glucocorticoid receptor antagonist binds preferentially to GR rather than the progesterone receptor (PR). In some embodiments, the specific glucocorticoid antagonist binds preferentially to GR rather than to the androgen receptor (AR). In some embodiments, the specific glucocorticoid antagonist binds preferentially to GR rather than to the estrogen receptor (ER).

In some embodiments, the specific glucocorticoid receptor antagonist binds to the GR with an association constant (Kd) that is at least 10-fold less than the Kd for AR or PR. In some embodiments, the specific glucocorticoid receptor antagonist binds to the GR with an association constant (Kd) that is at least 100-fold less than the Kd for AR or PR. In some embodiments, the specific glucocorticoid receptor antagonist binds to the GR with an association constant (Kd) that is at least 1000-fold less than the Kd for AR, PR or ER.

In some embodiments, the disorder or condition is a substance use disorder, which may be an addiction disorder. Addictive disorders, such as substance abuse and dependence, are common disorders that involve the overuse of alcohol or drugs. Substance abuse, as a disorder, refers to the abuse of illegal substances or the abusive use of legal substances (e.g., alcohol). Substance dependence is an addictive disorder that describes continued use of drugs or alcohol, even when significant problems related to their use have developed. Signs include an increased tolerance—that is, the need for increased amounts of the substance to attain the desired effect; withdrawal symptoms with decreased use; unsuccessful efforts to decrease use; increased time spent in activities to obtain the substance; withdrawal from social and recreational activities; and continued use of the substance even with awareness of the physical or psychological problems encountered by the extent of substance use. Chemical dependence is also an addictive disorder that describes the compulsive use of chemicals (usually drugs or alcohol) and the inability to stop using them despite all the problems caused by their use. The substances frequently abused, particularly by adolescents with addictive disorders, include, but are not limited to, alcohol, marijuana, hallucinogens, cocaine, amphetamines, opiates, anabolic steroids, inhalants, methamphetamine, or tobacco.

In some embodiments, the present invention provides a method of treating a substance use disorder, comprising administering to a subject in need thereof, a therapeutically effective amount of a pharmaceutical composition disclosed herein, thereby treating the substance use disorder.

In some embodiments, the present invention provides a method of treating fatty liver disease, comprising administering to a subject in need thereof, a therapeutically effective amount of a composition of the present invention, thereby treating fatty liver disease.

In some embodiments, the disorder or condition is the fatty liver disease is alcohol related liver disease (ARLD) or nonalcoholic fatty liver disease (NAFLD). In some embodiments, the alcohol related liver disease is alcohol fatty liver disease (AFL), alcoholic steatohepatitis (ASH) or alcoholic cirrhosis.

In some embodiments, the disorder or condition is non-alcoholic fatty liver disease. In some embodiments, the nonalcoholic fatty liver disease is nonalcoholic steatohepatitis (NASH) or nonalcoholic cirrhosis. In some embodiments, the disorder or condition is nonalcoholic steatohepatitis.

NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid receptor.

In some embodiments, the present invention provides a method of treating antipsychotic induced weight gain, comprising administering to a subject in need thereof, a therapeutically effective amount of a composition of the present invention, thereby treating antipsychotic induced weight gain.

VI. Examples

Example 1

Preparation of Compound I

Compound I can be prepared as described in U.S. Pat. No. 8,685,973, Example 6, Compound 3b.

Example 2

Preparation of Crystalline Compound I

Crystalline Compound I can be prepared as described in U.S. Provisional Application No. 63/020,919, filed May 6, 2020, titled "Polymorphs of Pyrimidine Cyclohexyl Glucocorticoid Receptor Modulators".

The crystalline Form B of Compound I can be prepared by the method described below.

Dichloromethane (8.4 volumes) is charged to the vessel, followed by the dry, crude Compound I based on its assay content relative to residual acetic acid which is determined by $^1$H-NMR.

Methanol (1.7 volumes) is then charged and the resulting mixture is then warmed to 30-35° C. to obtain a solution;

The resulting solution is polish-filtered into a second vessel, then the source vessel is washed with a mixture of dichloromethane (DCM) (2.6 volumes) and methanol (0.5 volumes) and transferred to the second vessel, affording a total batch volume of approximately 13.5 volumes;

The resulting solution is heated to reflux at atmospheric pressure (approximately 38 to 40° C.) and distilled to remove 20 volumes of solvent. Concurrent with the distillation, a solvent exchange is performed by the addition of methanol (approximately 1 volume) for each volume of distillate collected to maintain a total solvent volume of approximately 13-14 volumes during the distillation. The distillation temperature is increased as needed to maintain a reasonable distillation rate;

After approximately 3 volumes of solvent have been exchanged by methanol, the batch is seeded with a slurry containing approximately 0.05% wt/wt of recrystallized Compound I form B in approximately 0.025 volumes of methanol, then the batch is held for approximately 10 minutes while noting any changes in the batch appearance;

After completing the exchange the fourth volume of solvent with methanol, a second seeding operation is performed by again charging a slurry containing approximately 0.05% wt/wt of recrystallized Compound I form B in approximately 0.025 volumes of methanol, followed by maintaining the batch for approximately 10 minutes and noting any changes in the batch appearance;

Next a fifth volume of solvent is exchanged with methanol and the batch held for approximately 10 minutes, and the batch visually inspected to confirm whether crystallization has occurred. If crystallization has not occurred at this point a third seeding operation is then performed;

Once crystallization of the batch is confirmed the distillation and solvent exchange with methanol is continued until another 15 volumes of solvent is exchanged or a total of approximately 20 volumes of solvent has been collected since the dissolution of the crude Compound I;

Once the internal batch temperature has reached approximately 65° C. and has stabilized at approximately 64° C., another 4 volumes of solvent are collected to reduce the batch volume to approximately 10 volumes;

The resulting slurry is then cooled to approximately 10° C. over a minimum of 2 hours, then held at that temperature for at least 2 hours and filtered;

The original vessel is washed with approximately 2 volumes of methanol with stirring at approximately 10-15° C.;

The methanol is then transferred to the filter, allowed to soak on the filter cake, then removed under vacuum. This wash operation is repeated, then the solid is sampled for in-process control (IPC) analysis for wet cake purity of the solid;

The filter cake is then dried at ≤50° C. for up to 72 h, sampling after at least 12 h of drying time for IPC analysis to determine residual solvent content;

Once the IPC specifications for residual solvents are met, the solid is discharged into antistatic poly liners and weighed;

The recrystallized Compound I is then sieved to break up any large lumps of solid using an oscillating sieve fitted with a 2 mm sieve screen and processed at a target oscillation speed of 0.2 m/s;

The resulting sieved Compound I is transferred to liners and weighed then the recrystallized Compound I is sampled for analysis, including X-ray powder diffraction (XRPD) to confirm that the batch of Compound I obtained as described above is consistent with polymorphic form B.

Example 3

Formulations of Compound I

Tablet formulations were prepared using the amounts described in the tables below. For example, formulation D3, having a unit dose of 150 mg Compound I and a tablet weight of 656 mg, was prepared as follows.

Preparation of Intermediate Mixture (Spray-Dried Mixture). Compound I, Eudragit L100, and optionally sodium lauryl sulfate, were dissolved in methanol and dichloromethane. Compound I, Eudragit L100, and optionally sodium lauryl sulfate may comprise between 5% to 7% of the total solution.

The resulting solution was spray dried using process conditions specific to the equipment utilized. When using a GEA Niro Mobile Minor, the solution was sprayed at a rate of 120 g/min, utilizing a drying gas flow rate of 1300 g/min and inlet and outlet temperatures of 86° C. and 40° C., respectively. Conversely, when using a small lab scale spray dryer, the solution was sprayed at a rate of 200 g/min, utilizing a drying gas flow rate of 3300 g/min and inlet and outlet temperatures of 65° C. and 30° C., respectively.

Upon completion of spray drying, a secondary drying process was performed to remove excess residual solvents from the intermediate mixture. Secondary drying was performed in a convection tray dryer operating at temperatures between 40° C. and 60° C., with a total drying duration dictated by removal of residual solvents to predefined levels.

Preparation of Intragranular Mixture. The Intermediate Mixture and intragranular materials (sustaining polymer, filler, disintegrant, glidant) were blended at 9 RPM for 7 minutes in a 200 L bin. The lubricant (magnesium stearate) was then added to the bin and the contents were blended at 9 RPM for 5 minutes. The blended mixture was then roller compacted using a Gerteis Roller Compactor using a press force of 3.0 kN/cm and roll speed of 2 RPM.

Preparation of Extragranular Mixture. The Intragranular Mixture and extragranular materials (distintegrant, glidant) were blended at 9 RPM for 20 minutes in a 200 L bin. The lubricant (magnesium stearate) was then added to the bin and the contents were blended at 9 RPM for 5 minutes.

Preparation of Tablets. The extragranular mixture was then compressed into core tablets using a Korsch XM12 rotary tablet press. Optionally, the core tablets may be film-coated using an aqueous or solvent based colorant solution.

| Function | Ingredient | C1 (% w/w) | D1 (% w/w) | D2 (% w/w) | D3 (% w/w) | D3A (% w/w) |
|---|---|---|---|---|---|---|
| Intermediate | | | | | | |
| Active agent | Compound I | 29.97% | 27.31% | 27.31% | 22.84% | 22.84% |
| | Eudragit L100 | 29.97% | 27.31% | 27.31% | 22.84% | 22.84% |
| | Sodium Lauryl Sulfate (SLS) | 1.85% | 1.69% | 1.69% | 1.41% | 1.41% |
| Intragranular | | | | | | |
| Sustaining Polymer | HPMCAS-H | — | 14.0% | 14.0% | 23.0% | 23.0% |
| Filler | Microcrystalline Cellulose (Avicel PH102) | 27.7% | 19.2% | 23.2% | 19.4% | 18.4% |
| Disintegrant | Croscarmellose Sodium (Ac-Di-Sol) | 6.0% | 6.0% | 3.0% | 6.0% | 6.0% |
| Glidant | Colloidal Silicon Dioxide (Cab-O-Sil MP5) | — | — | — | — | 0.50% |
| Lubricant | Magnesium Stearate | 0.25% | 0.25% | 0.25% | 0.25% | 0.25% |
| Extragranular | | | | | | |
| Disintegrant | Croscarmellose Sodium (Ac-Di-Sol) | 4.0% | 4.0% | 3.0% | 4.0% | 4.0% |
| Glidant | Colloidal Silicon Dioxide (Cab-O-Sil MP5) | — | — | — | — | 0.50% |
| Lubricant | Magnesium Stearate | 0.25% | 0.25% | 0.25% | 0.25% | 0.25% |
| | Tablet Weight (mg) | 1000 | 1098 | 1098 | 656 | 656 |
| | Unit Dosage (mg) | 300 | 300 | 300 | 150 | 150 |

| Function | Ingredient | C1 (% w/w) | E1 (% w/w) | E1A (% w/w) | E2 (% w/w) | E3 (% w/w) |
|---|---|---|---|---|---|---|
| Intermediate | | | | | | |
| Active agent | Compound I | 29.97% | 25.0% | 22.87% | 26.09% | 27.28% |
| | Eudragit L100 | 29.97% | 25.0% | 22.87% | 26.09% | 27.28% |
| | Sodium Lauryl Sulfate (SLS) | 1.85% | — | — | — | — |

-continued

| | | Intragranular | | | | |
|---|---|---|---|---|---|---|
| Sustaining Polymer | HPMCAS-H | — | 25.0% | 22.87% | 26.09% | 20.46% |
| Filler | Microcrystalline Cellulose (Avicel PH 102) | 27.7% | 13.75% | 19.9% | 14.48% | 13.74% |
| Disintegrant | Croscarmellose Sodium (Ac-Di-Sol) | 6.0% | 6.0% | 6.0% | 3.0% | 6.0% |
| Glidant | Colloidal Silicon Dioxide (Cab-O-Sil MP5) | — | 0.50% | 0.50% | 0.50% | 0.50% |
| Lubricant | Magnesium Stearate | 0.25% | 0.25% | 0.25% | 0.25% | 0.25% |
| | | Extragranular | | | | |
| Disintegrant | Croscarmellose Sodium (Ac-Di-Sol) | 4.0% | 4.0% | 4.0% | 3.0% | 4.0% |
| Glidant | Colloidal Silicon Dioxide (Cab-O-Sil MP5) | — | 0.25% | 0.50% | 0.25% | 0.25% |
| Lubricant | Magnesium Stearate | 0.25% | 0.25% | 0.25% | 0.25% | 0.25% |
| | Tablet Weight (mg) | 1000 | 600 | 656 | 575 | 550 |
| | Unit Dosage (mg) | 300 | 150 | 150 | 150 | 150 |

| Function | Ingredient | Original (% w/w) |
|---|---|---|
| | Intermediate | |
| Active agent | Compound I | 9.09% |
| | Eudragit L100 | 9.09% |
| | Sodium Lauryl Sulfate (SLS) | 0.57% |
| | Intragranular | |
| Sustaining Polymer | HPMCAS-H | — |
| Filler | Mannitol (Parteck M200) | 71.8% |
| Disintegrant | Croscarmellose Sodium (Ac-Di-Sol) | 8.29% |
| Glidant | Colloidal Silicon Dioxide (Cab-O-Sil MP5) | — |
| Lubricant | Magnesium Stearate | 0.66% |
| | Extragranular | |
| Disintegrant | Croscarmellose Sodium (Ac-Di-Sol) | — |
| Glidant | Colloidal Silicon Dioxide (Cab-O-Sil MP5) | — |
| Lubricant | Magnesium Stearate | 0.5% |
| | Tablet Weight (mg) | 1100 |
| | Unit Dosage (mg) | 100 |

Example 4

Monkey PK Study

Four cynomolgus monkeys were assigned to study. The same animals were used for each phase with a minimum 7 day washout period between dosing for each phase. All animals were fasted for at least 8 hours prior to dosing and through the first 4 hours of blood sample collection (food was returned within 30 minutes following collection of the last blood sample at the 4 hour collection interval, where applicable).

Each animal received an oral tablet dose of the appropriate test article formulation as outlined in the following study design table. The gavage tube was rinsed with approximately 10 mL of tap water following dosing (prior to removal of the gavage tube).

The data are summarized in FIG. 6.

| Group | Test Article | No. of Males | Dose Route | Formulation | Dose Level (mg/animal) | Dose Amount (tablets/animal) | Collection Intervals |
|---|---|---|---|---|---|---|---|
| | | | | PHASE 1 | | | |
| 1 | Compound I (immediate release 100 mg) | 4 | Oral Tablet | a | 300 | 3 | Blood[b] |
| | | | | PHASE 2 | | | |
| 1 | Compound I (immediate release 300 mg) | 4 | Oral Tablet | a | 300 | 1 | Blood[b] |

-continued

| Group | Test Article | No. of Males | Dose Route | Formulation | Dose Level (mg/animal) | Dose Amount (tablets/animal) | Collection Intervals |
|---|---|---|---|---|---|---|---|
| PHASE 3 | | | | | | | |
| 1 | Compound I (immediate release 300 mg) | 4 | Oral Tablet | a | 300 | 1 | Blood[b] |
| PHASE 4 | | | | | | | |
| 1 | Compound I (immediate release 150 mg) | 4 | Oral Tablet | A | 300 | 2 | Blood[b] | a All tablet formulations were provided pre-formulated and were be used as received.
[b]Blood samples were collected at 0.5 (30 min.), 1, 2, 4, 8, 12, 24 and 48 hours postdose.

Example 5

Monkey PK Study

Four cynomolgus monkeys were assigned to study. The same animals were used for each phase with a minimum 7 day washout period between dosing for each phase. All animals were fasted for at least 8 hours prior to dosing and through the first 4 hours of blood sample collection (food was returned within 30 minutes following collection of the last blood sample at the 4 hour collection interval, where applicable).

Each animal in received an oral tablet dose of the appropriate test article formulation as outlined in the following study design table. The gavage tube was rinsed with approximately 10 mL of tap water following dosing (prior to removal of the gavage tube).

The data are summarized in FIG. 7.

| Group | Test Article | No. of Males | Dose Route | Formulation | Dose Level (mg/animal) | Dose Amount (tablets/animal) | Collection Intervals |
|---|---|---|---|---|---|---|---|
| PHASE 1 | | | | | | | |
| 1 | Compound I (C1) | 4 | Oral Tablet | a | 300 | 1 | Blood[b] |
| PHASE 2 | | | | | | | |
| 1 | Compound I (D3) | 4 | Oral Tablet | a | 300 | 2 | Blood[b] |
| PHASE 3 | | | | | | | |
| 1 | Compound I (E1) | 4 | Oral Tablet | a | 300 | 2 | Blood[b] | a All tablet formulations will be provided pre-formulated and will be used as received.
[b]Blood samples will be collected at 0.5 (30 min.), 1, 2, 4, 8, 12, 24 and 48 hours postdose.

Example 6

Human PK Study—100 Mg Tablets

An open label study was conducted in 6 heathy volunteers to assess the safety, tolerability and pharmacokinetics of miricorilant 100 mg tablets. A single oral dose of miricorilant 200 mg as 2×100 mg tablets was administered 30 minutes after the consumption of breakfast. Intensive pharmacokinetic (PK) samples were collected at 1, 2, 4, 8, 12, 16, 24, 36, 48, 72 and 96 hours post-dose. The plasma concentrations of miricorilant were determined using a validated LC/MS bioanalytical assay. The geometric mean $C_{max}$ was 184 ng/mL (at 4 hours post-dose), and the geometric mean $AUC_{0-24}$ was 2270 ng·h/mL.

Example 7

Human PK Study—150 and 300 Mg Tablets

A randomized study was conducted in 12 healthy volunteers to assess the safety, tolerability and PK of miricorilant C1 300 mg tablets and D3 150 mg tablets. Subjects were randomized 1:1 to receive either a single dose of miricorilant 900 mg as 3×C1 300 mg tablets or a single dose of miricorilant 300 mg as 2×D3 150 mg tablets. Both dose regimens were administered within 30 minutes after the consumption of breakfast. Intensive pharmacokinetic (PK) samples were collected at 1, 2, 4, 8, 12, 16, 24, 36, 48 and 72 post-dose. The plasma concentrations of miricorilant were determined using a validated LC/MS bioanalytical assay. For the 900 mg dose of C1 300 mg tablets, the geometric mean $C_{max}$ was 408 ng/mL (at 4 hours post-dose), and the geometric mean $AUC_{0-last}$ was 6680 ng·h/mL. For the 300 mg dose of the D3 150 mg tablets the geometric mean $C_{max}$ was 265 ng/mL (at 4 hours post-dose), and the geometric mean $AUC_{0-last}$ was 3540 ng·h/mL. Thus, although the difference in dose was 3 fold (900 mg C1 tablets compared with 300 mg D3 tablets) the difference AUC was less than 2 fold, indicating superior performance of the D3 tablets as compared to the C1 tablets.

Although the foregoing invention has been described in some detail by way of illustration and example for purposes of clarity of understanding, one of skill in the art will appreciate that certain changes and modifications may be practiced within the scope of the appended claims. In addition, each reference, including all of the U.S. patents, U.S. patent application publications, U.S. patent applications, foreign patents, foreign patent applications and nonpatent publications referred to in this specification are incorporated herein by reference, in their entirety, to the extent not inconsistent with the present description. Where a conflict exists between the instant application and a reference provided herein, the instant application shall dominate.

What is claimed is:

1. A composition comprising:
Compound I, (E)-6-(4-Phenylcyclohexyl)-5-(3-trifluoromethylbenzyl)-1H-pyrimidine-2,4-dione:

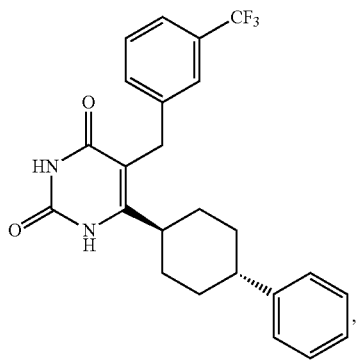 [SMILES: O=c1[nH]c(=O)c(Cc2cccc(C(F)(F)F)c2)c([C@H]2CC[C@H](c3ccccc3)CC2)[nH]1]

in an amount from 20.0 to 28.0% (w/w);
a poly[(methyl methacrylate)-co-(methacrylic acid)] in an amount from 20.0 to 28.0% (w/w);
sodium lauryl sulfate in an amount from 0.5 to 5.0% (w/w);
a sustaining polymer which is hydroxypropyl methylcellulose acetate succinate (HPMCAS), in an amount from 10.0 to 28.0% (w/w);
microcrystalline cellulose in an amount from 10.0 to 25.0% (w/w); and
croscarmellose sodium (Ac-Di-Sol) in an amount from 5.0 to 11.0% (w/w).

2. The composition of claim 1, wherein the poly[(methyl methacrylate)-co-(methacrylic acid)] has a methyl methacrylate to methacrylic acid ratio of about 1:1.

3. The composition of claim 1, wherein the sustaining polymer is hydroxypropyl methylcellulose acetate succinate high fine grade (HPMCAS-H).

4. The composition of claim 2, comprising
Compound I, in an amount from 22.0 to 28.0% (w/w);
the poly[(methyl methacrylate)-co-(methacrylic acid)] having a methyl methacrylate to methacrylic acid ratio of about 1:1, in an amount from 22.0 to 28.0% (w/w);
sodium lauryl sulfate in an amount from 0.5 to 5.0% (w/w)
hydroxypropyl methylcellulose acetate succinate high fine grade in an amount from 13.0 to 28.0% (w/w);
microcrystalline cellulose (Avicel PH102) in an amount from 13.0 to 20.0% (w/w); and
croscarmellose sodium (Ac-Di-Sol) in an amount from 5.0 to 11.0% (w/w).

5. The composition of claim 1, further comprising sodium lauryl sulfate in an amount from 1.25 to 1.75% (w/w).

6. The composition of claim 1, further comprising sodium lauryl sulfate in an amount from 1.3 to 1.5% (w/w).

7. The composition of claim 1, comprising
Compound I, in an amount of about 22.8% (w/w);
the poly[(methyl methacrylate)-co-(methacrylic acid)] having a methyl methacrylate to methacrylic acid ratio of about 1:1, in an amount of about 22.8% (w/w);
sodium lauryl sulfate in an amount of about 1.4% (w/w);
hydroxypropyl methylcellulose acetate succinate high fine grade in an amount of about 23.0% (w/w);
microcrystalline cellulose (Avicel PH102) in an amount of about 19.4% (w/w);
croscarmellose sodium (Ac-Di-Sol) in an amount of about 10.0% (w/w); and
magnesium stearate in an amount of about 0.5% (w/w).

8. The composition of claim 1, further comprising colloidal silicon dioxide (Cab-O-Sil MP5) in an amount from 0.1 to 2.0% (w/w).

9. The composition of claim 8, wherein the colloidal silicon dioxide (Cab-O-Sil MP5) is present in an amount from 0.50 to 1.5% (w/w).

10. The composition of claim 1, comprising
Compound I, in an amount of about 22.8% (w/w);
the poly[(methyl methacrylate)-co-(methacrylic acid)] having a methyl methacrylate to methacrylic acid ratio of about 1:1, in an amount of about 22.8% (w/w);
sodium lauryl sulfate in an amount of about 1.4% (w/w);
hydroxypropyl methylcellulose acetate succinate high fine grade in an amount of about 23.0% (w/w);
microcrystalline cellulose (Avicel PH102) in an amount of about 18.4% (w/w);
croscarmellose sodium (Ac-Di-Sol) in an amount of about 10.0% (w/w);
colloidal silicon dioxide (Cab-O-Sil MP5) in an amount of about 1.0% (w/w); and
magnesium stearate in an amount of about 0.5% (w/w).

11. The composition of claim 8, wherein the microcrystalline cellulose (Avicel PH102) in an amount from 10.0 to 30.0% (w/w).

12. The composition of claim 11, wherein the microcrystalline cellulose (Avicel PH102) in an amount from 13.0 to 20.0% (w/w).

13. The composition of claim 11, wherein the weight ratio of Compound I to the poly[(methyl methacrylate)-co-(methacrylic acid)] is about 1:1.

14. The composition of claim 11, comprising
Compound I, in an amount of about 25.0% (w/w);
the poly[(methyl methacrylate)-co-(methacrylic acid)] having a methyl methacrylate to methacrylic acid ratio of about 1:1, in an amount of about 25.0% (w/w);
hydroxypropyl methylcellulose acetate succinate high fine grade in an amount of about 25.0% (w/w);
microcrystalline cellulose (Avicel PH102) in an amount of about 13.75% (w/w);
croscarmellose sodium (Ac-Di-Sol) in an amount of about 10.0% (w/w);
colloidal silicon dioxide (Cab-O-Sil MP5) in an amount of about 0.75% (w/w); and
magnesium stearate in an amount of about 0.5% (w/w).

15. The composition of claim 11, comprising
Compound I, in an amount of about 22.9% (w/w);
the poly[(methyl methacrylate)-co-(methacrylic acid)] having a methyl methacrylate to methacrylic acid ratio of about 1:1, in an amount of about 22.9% (w/w);
hydroxypropyl methylcellulose acetate succinate high fine grade in an amount of about 22.9% (w/w);
microcrystalline cellulose (Avicel PH102) in an amount of about 19.8% (w/w);
croscarmellose sodium (Ac-Di-Sol) in an amount of about 10.0% (w/w);
colloidal silicon dioxide (Cab-O-Sil MP5) in an amount of about 1.0% (w/w); and
magnesium stearate in an amount of about 0.5% (w/w).

* * * * *